US00PP08086P

United States Patent [19]

Nelson et al.

[11] Patent Number: Plant 8,086

[45] Date of Patent: Jan. 5, 1993

[54] STRAWBERRY PLANT NAMED 'PSI-130'

[75] Inventors: Steven D. Nelson; Michael D. Nelson, both of Watsonville; Daniel T. Schmida, Aptos, all of Calif.

[73] Assignees: Plant Sciences, Inc.; Coast Cooling, Inc., both of Watsonville, Calif.

[21] Appl. No.: 637,112

[22] Filed: Jan. 3, 1991

[51] Int. Cl.[5] ..... A01H 5/00

[52] U.S. Cl. ..... Plt./49

[58] Field of Search ..... Plt./48, 49

[56] References Cited

U.S. PATENT DOCUMENTS

P.P. 4,487 11/1979 Bringhurst et al. ..... Plt. 49
P.P. 4,538 5/1980 Bringhurst et al. ..... Plt. 49
P.P. 5,262 7/1984 Voth et al. ..... Plt. 48
P.P. 5,266 7/1984 Bringhurst et al. ..... Plt. 49
P.P. 6,558 1/1989 Bringhurst et al. ..... Plt. 49
P.P. 7,172 2/1990 Voth et al. ..... Plt. 49

*Primary Examiner*—James R. Feyrer
*Attorney, Agent, or Firm*—Foley & Lardner

[57] ABSTRACT

This invention relates to a new and distinct day neutral type strawberry variety named 'PSI-130'. The new variety produces a relatively high fruit yield, comparable to that of the standard cultivar 'Selva'. The variety is characterized by its medium sized, light colored fruit which is smoother and more conic than that of 'Selva'. The fruit shelf life is comparable to that of the standard cultivars 'Selva' and 'Muir'. The plant is similar in appearance to 'Selva', yet slightly less vigorous.

4 Drawing Sheets

INTRODUCTION

This invention relates to a new and distinct day neutral type strawberry variety designated 'PSI-130' (hereafter '130'). The botanical name of the variety is *F. Chiloensis* Duch. var. *ananasa*. The new variety resulted from a breeding program initiated jointly by Plant Sciences, Inc. and Coast Cooling, Inc., both of Watsonville, Calif., with the goal of developing new and distinct strawberry varieties.

Variety '130' was discovered as a seedling when it first fruited in a breeding plot established in November, 1987 on a ranch in Watsonville, Calif. provided by Well-Pict, Inc. The seedling had been grown and asexually propagated by stolons during the spring and summer of 1987 in a seedling nursery located in Lassen County, Calif. After being selected in the spring of 1988, clones of the new variety which had been asexually produced in 1987 were further propagated in the nursery and extensively tested the following fruiting season (1988-1989). This asexual propagation has demonstrated that the combination of characteristics disclosed herein for the new variety are fixed and retained through successive generations of asexual reproduction.

The following characteristics are particularly distinguishing and outstanding in '130';

1. Day neutral type fruiting habit.
2. High total marketable fruit yield.
3. Medium sized, light colored fruit having good flavor, juiciness and gloss.
4. Vigorous plant when given proper chilling; slighly less vigorous and darker than 'Selva' (U.S. Plant Pat. No. 5,266) and slightly lighter than 'PSI-118'.
5. Greater tolerance to rain than 'PSI-118', resulting in less fruit cracking and fungal infection.

DESCRIPTION OF THE PHOTOGRAPHIC DRAWINGS

The accompanying photographs, taken in both greenhouse filtered and outdoor field sunlight in Watsonville, Calif., show typical specimens of '130' at various stages of development.

Sheet 1 shows typical early season plant parts of the new variety, including leaves, individual flowers, inflorescences and mature fruit. The underside of a mature leaflet plug the upper surface of a mature trifoliate leaf are pictured, showing typical leaflet size, color, venation and serration. Two inflorescences are shown, one with all immature fruit, and the other with three simultaneously matured berries. Also pictured are cross-sectional and longitudinal view of mature fruit, illustrating typical flesh coloring, conspicuous core and core cavity.

Sheet 2 shows typical plant growth, flowering and fruiting characteristics in early August. The photograph illustrates that inflorescences are moderately long and semi-erect, falling to the sides of the bed as fruit matures.

Sheet 3 is a close-up view of fruit harvested on June 27, 1990 and packed in a standard twelve dry pint crate. As seen, '130' fruit is relatively light in color, ranging in shape from mostly medium conic to somewhat wedgy with some longitudinal creases.

FIG. 1 depicts isozyme banding patterns for varieties '130' and 'selva' and establishes their separate identities.

FRUIT PRODUCTION CHARACTERISTICS

Variety '130' is primarily adapted to the climate and growing conditions of the central coast of California, where it was selected. This region provides the variety with the necessary cold winter temperatures required for it to produce a vigorous plant and remain in fruit production from April through October. The nearby Pacific ocean provides the humidity and cool temperatures needed to maintain fruit quality during the summer production months.

Variety '130' has a vernalization (chilling) requirement comparable to that of 'Selva'. Winter planted '130' begins fruiting early to mid April, about the same time as 'Selva'. Initial yield studies have shown that the new variety is capable of producing a total marketable fruit yield at least comparable to, and experimentally up to 13 percent greater than that of 'Selva' and 38 percent greater than that of 'Muir' (U.S. Plant Pat. No. 6,558), with a season average fruit size about 11 percent smaller than that of both standard cultivars (Table 1). The studies have shown that 'Selva' produces considerably more fruit than '130' in May, while '130' produces considerably more fruit than 'Selva' from June through October.

TABLE 1

1989 marketable fruit yield and size comparison of high elevation (Susanville, California) '130' plants with standard cultivars dug October 20, 1988 and planted November 11, 1988 in Watsonville, California.

| MONTHLY YIELDS - GRAMS/PLANT | | | | | |
|---|---|---|---|---|---|
| CULTIVAR | 4/30 | 5/31 | 6/30 | 7/31 | 8/31 |
| '130' | 51 | 83 | 149 | 319 | 239 |
| 'SELVA' | 78 | 143 | 66 | 321 | 218 |
| 'MUIR' | 19 | 84 | 96 | 203 | 161 |

| CULTIVAR | 9/30 | 10/31 | TOTAL G/PL | SIZE G/FR |
|---|---|---|---|---|
| '130' | 229 | 58 | 1128 | 19.3 |
| 'SELVA' | 113 | 39 | 978 | 20.2 |
| 'MUIR' | 109 | 20 | 692 | 20.1 |

VARIETAL DESCRIPTION

Following is a detailed description of the new variety based on observations taken in July and August, 1990 from plants that were planted in November, 1989, in Watsonville, Calif. Color terminology is in accordance with the Munsell Book of Colors, Munsell color, Baltimore, Md. (1976).

Parentage: Variety '130' is the result of a cross of 'Selva' × 'Pajaro' (U.S. Plant Pat. No. 4,538), made in 1986.

FRUIT.

Fruit shape is characteristically medium to long conic, similar to 'Pajaro', but somewhat flat and wedgy, unlike 'Pajaro' but similar to 'Selva', having longitudinal creases. The new variety produces fewer wedge-shaped fruit with creases that are slightly shallower than that of 'Selva', giving the fruit a smoother appearance. The fruit have less rounded shoulders than 'PSI-118'. The achenes are typically positioned flush with the berry surface with few exerted and few embedded. Typically, the achenes are spaced evenly over the berry surface, with very few fruit having seedy tips. Fruit is moderately juicy, comparable to that of 'Selva', and slightly glossier than both 'Selva' and 'Muir'. The flavor is comparable to that of 'Selva'. The fruit typically have a conspicuous core and hollow core cavity with the flesh being lighter in color than the outer surface. Fruit quality characteristics including color, soluble solids, firmness and calyx diameter are compared with those of 'Selva' and 'Muir' in Table 2.

TABLE 2

Comparison of mid-summer 1990 fruit quality characteristics of '130', 'Selva' and 'Muir' from fruit produced in Watsonville, California

| CULTIVAR | SURFACE COLOR (MUNSELL) | | % SOL. SOLIDS RANGE | % SOL. SOLIDS AVERAGE |
|---|---|---|---|---|
| '130' | 7.5R to 7.5R | 5/14 4/14 | 6.5–7.3 | 7.0 |
| 'SELVA' | 7R | 4/11* | 7.2–7.8 | 7.4 |
| 'MUIR' | 7R | 4.5/13* | 7.5–8.3 | 7.8 |

| CULTIVAR | FIRMNESS RATING (0-10) | CALYX DIAMETER (MM) RANGE | CALYX DIAMETER (MM) AVERAGE |
|---|---|---|---|
| '130' | 7.9 | 27–52 | 35 |
| 'SELVA' | 8.8 | 26–42 | 34 |
| 'MUIR' | 8.1 | 23–41 | 32 |

*'Selva' and 'Muir' fruit surface color according to Voth et al., U.S. Pat. No. 7,172 ('Irvine') 1990.

The skin surface and flesh are considered light, slightly lighter than 'Muir' or 'Selva'. Fruit typically ripen from the base to the tip. With reduced light conditions, such as caused by heavy foliage, fruit may become very light, tending toward albinism, a physiological disorder causing the fruit surface to become very pale with the achenes sunken and flesh protruding, resulting in weak fruit which is very susceptible to bruising and bleeding. Refractometer readings indicate that fruit have a slightly less percentage soluble solids than 'Selva' and 'Muir'. Fruit is slightly less firm than that of 'Selva', comparable to that of 'Muir' and stores and ships about as well as the standard cultivars. The calyx is medium in size, comparable to that of 'Selva' and 'Muir', with a slightly greater range in diameter. The calyx consists of an average of 12 sepals and attached firmly, even with the base of the fruit, sometimes on a neck, especially late in the season. The sepals are elliptical to narrow ovate in shape, typically with an actue apex, sometimes with a blunt apex, frequently overlapping with few serrations.

PLANT

Plants are similar in appearance to those of 'Selva', but slightly less vigorous. The crown branches similarly to 'Selva' and 'Muir' and attaches to the soil as firmly as do the two standard cultivars. Plant foliage is semi-erect, similar to 'Selva', less erect than 'Muir' and considerably less erect than 'Irvine' (U.S. Plant Pat. No. 7,172).

Foliage.

Leaf characteristics are compared with those of 'Selva' and 'Muir' in Table 3.

TABLE 3

Comparison of mid-summer 1990 leaf characteristics of '130', 'Selva' and 'Muir' from plants grown in Watsonville, California

| CHARACTER | '130' | 'SELVA' | 'MUIR' |
|---|---|---|---|
| Munsell Leaf Color (Upper Surface) | 7.5 GY 3/6 | 7.5 GY 4/4 | 2.5 GY 4/3 |
| Petiole Length (CM) | 23.8 | 22.5 | 22.0 |
| Petiolule Length (MM) | 11.6 | 13.7 | 6.7 |
| Terminal Leaflet Size - L × W (CM) | 9.2 × 8.0 | 9.3 × 8.2 | 8.9 × 8.3 |
| Terminal Leaflet Ratio (L/W) | 1.14 | 1.13 | 1.07 |
| Terminal Leaflet Basal Angle (Degrees) | 49.8 | 50.4 | 63.2 |
| No. of Serrations (½ Terminal Leaflet) | 10.0 | 11.1 | 10.7 |
| Serration Depth (MM) | 3.8 | 4.7 | 5.6 |

Leaves are slightly darker and less gray than those of 'Selva' and less yellow than those of 'Muir'. Petioles are comparable in length to those of the standard cultivars. Terminal leaflet petiolules are slightly shorter than those of 'Selva', but considerably longer than those of 'Muir'. Terminal leaflets are comparable in length to those of 'Selva', slightly longer than those of 'Muir', and narrower than those of both the standard cultivars. Terminal leaflet shape is described by the ratio of length/width and the basal angle, both of which indicate that '130' terminal leaflets are nearly the same shape as those of 'Selva' and considerably less round than those of 'Muir'. Terminal leaflets have slightly fewer serrations per half terminal leaflets than 'Salva' and 'Muir'. The serrations are shallower than those of 'Selva' and 'Muir', having moderately acute, rarely overlapping apexes. Bract leaflets occur on fewer than half of the petioles, and may occur singly or in pairs. Pubescence on petioles grow at about a 60° angle to the petioles, less perpendicular than that of 'PSI-118'. Light pubescence is also present on the upper and lower leaf surfaces, irregularly parallel to these surfaces. Leaf surface is moderately rugose.

Isozymes in Leaf Extract

Studies of protein polymorphism by the starch gel electrophoresis method were carried out to characterize this newly developed variety and distinguish it from other varieties. The following isozymes were extracted from young leaves and characterized: phosphoglucoisomerase (PGI:EC 5.3.1.9), phosphoglucomutase (PGM: EC 2.7.5.1) and leucine aminopeptidase (LAP: EC 3.4.11.1). The plant material used was both field and greenhouse grown in Watsonville, Calif. Newly matured leaves (lg fresh weight) were collected in the morning, held at 4°-8° C. and analyzed within 24 hours. Gel and electrode buffers for the enzyme systems analyzed are given in Table 4. Electrophoresis specifications for these enzyme systems are given in Table 5. The techniques and stains used were described in Arulsekar and Parfitt. *Hort Sci.* (1986).

TABLE 4 gel and electrode buffers for *Fragaria* enzyme systems

| SYSTEM | GEL BUFFER | G/L | pH | ELECTRODE BUFFER | G/L | pH |
|---|---|---|---|---|---|---|
| A | TRIS BASE | 6.5 | 8.3 | LITHIUM HYDROXIDE | 1.2 | 8.3 |
| | CITRIC ACID (MONOHYD.) | 1.5 | | BORIC ACID | 12.0 | |
| B | DL-HISTIDINE HCL (MONOHYD.) | 1.2 | 7.0 | TRIS BASE | 16.5 | 7.0 |
| | | | | CITRIC ACID (MONOHYD.) | 9.0 | |

TABLE 5

*Fragaria* electrophoresis specifications

| SYSTEM | ENZYME | pH | CURRENT | GEL SLICE # |
|---|---|---|---|---|
| A | PGI | 8.3 | 275V | 2 |
| A | LAP | 8.3 | 275V | 4 |
| B | PGM | 7.0 | 150V | 3 |

Following electrophoresis, the gel was sliced into equal slices and stained for each enzyme system. Banding patterns were interpreted as they developed and gel slices were fixed in 50% glycerol. The banding pattern codes referred to are those of Bringhurst et al. (1981). The isozyme banding patterns for the three enzyme systems are compared to those of 'Selva' in the FIG. 6, and are compared to those of 'Selva', 'Chandler', 'Pajaro' and 'Douglas' in Table 6. Variety '130' has a pattern combination (A4, B3, C2) which separates it from all University of California patented varieties except 'Fern', based on the pattern C2 for PGM.

TABLE 6

| CULTIVAR | PGI | LAP | PGM |
|---|---|---|---|
| '130' | A4 | B3 | C4 |
| 'SELVA' | A2 | B3 | C2 |
| 'MUIR' | A2 | B1 | C2 |
| 'IRVINE' | A3 | B1 | C2 |
| 'CHANDLER' | A1 | B3 | C1 |
| 'PAJARO' | A4 | B3 | C1 |
| 'DOUGLAS' | A3 | B3 | C1 |

INFLORESCENCE

Inflorescences are morphologically very similar to those of 'Selva'. The prolific flower clusters are borne on semi-erect peduncles averaging 16.7 cm in length, slightly shorter than those of 'Selva' (averaging 18.3 cm long), yet slightly longer than those of Muir (averaging 15.0 cm long). Typically, two to three secondary peduncles and a solitary pedicel bearing the primary berry originate at the apex of the primary peduncle. The pedicel bearing the primary berry may originate from the axil of one of the secondary peduncles or branch from the base of one of the secondary peduncles, the latter shown in the inflorescence at the center of Sheet 2. Tertiary penduncles typically originate at the apex of the secondary peduncles. Secondary and tertiary berries are borne on pedicels which are typically longer than the pedicel bearing the primary berry. Sometimes, the inflorescence does not produce a solitary pedicel bearing a primary berry, as shown in the inflorescence at the right of Sheet 1. In this case, primary and secondary fruit borne on pedicels originating at the apex of secondary peduncles may ripen simultaneously.

Flowers are moderately large, producing ample pollen for good pollination for the entire season. Flowers may or may not be seen above the plant canopy, having an average of six to seven obovate shaped petals per flower averaging 11.8 mm long and 12.1 mm wide. Typically, a bract leaflet ranging in shape from elliptical to ovate is borne on a small petiolule which originates at the primary peduncle apex alongside the base of one of the secondary peduncles. Sometimes, this bract leaflet may branch forming a trifoliate, rarely a two foliate. In addition, bracts typically originate at the primary, secondary and tertiary peduncle apices. Pubescence on the primary peduncle grow at about a 60° angle to the peduncle, less perpendicular than that of 'PSI-118'.

Stolons

Stolon production in nursery plants is very good, comparable to 'Selva'. The new variety produces about half as many stolons as 'Selva' and 'Muir' in the fruiting field if given more than optional chilling for maximum fruit yields.

PEST REACTIONS

Variety '130' may not be resistant to any known insect or disease pests common in California. It is known to be moderately susceptible to the two-spotted spider mite. It is also known to be moderately susceptible to powdery mildew and grey fruit mold. From field observations, the variety does not appear to be susceptible to the virus disease complexes (including 'Mild Yellow Edge') common in California. It has not been tested for susceptibility to *P. cactorum* or *C. acutatum*.

This new variety may vary slightly in detail, depending upon weather, soil, location and evaluation date.

We claim:

1. A new distinct strawberry variety, as herein described and illustrated.

* * * * *

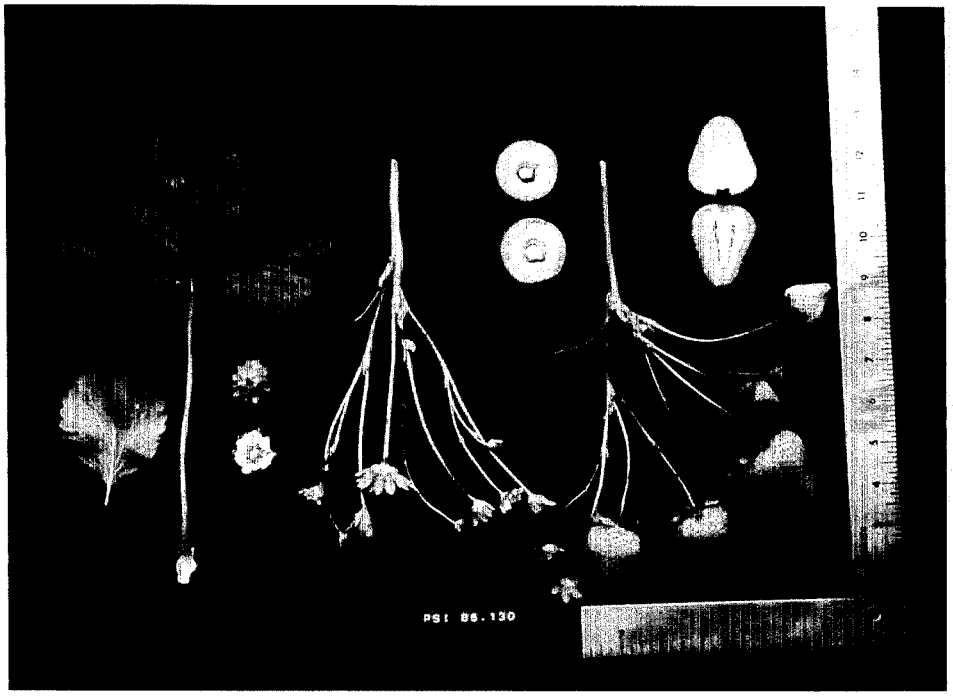
PGI 86.130

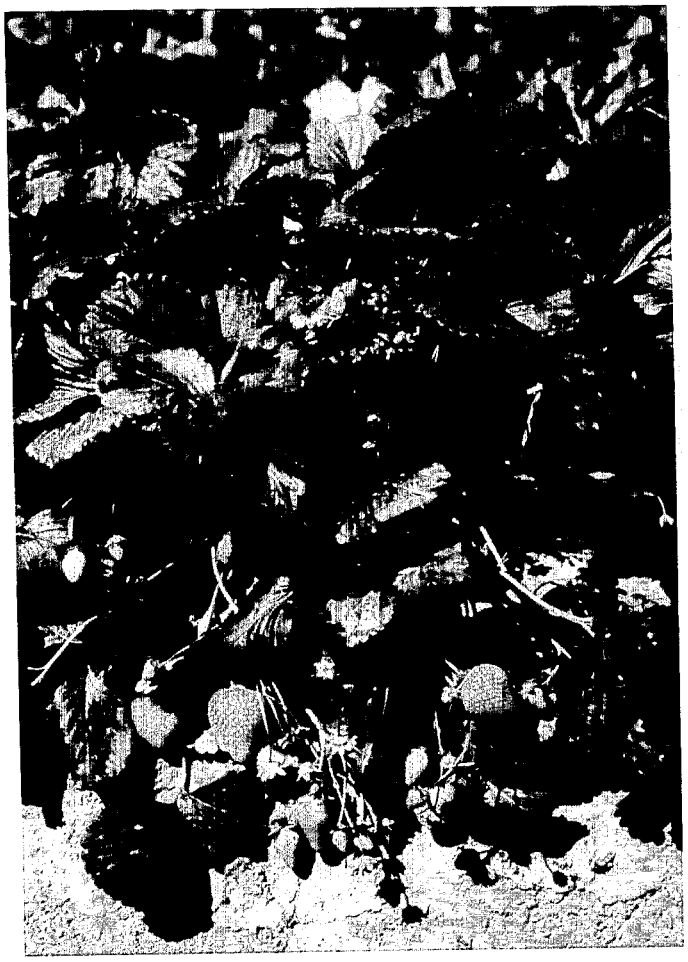

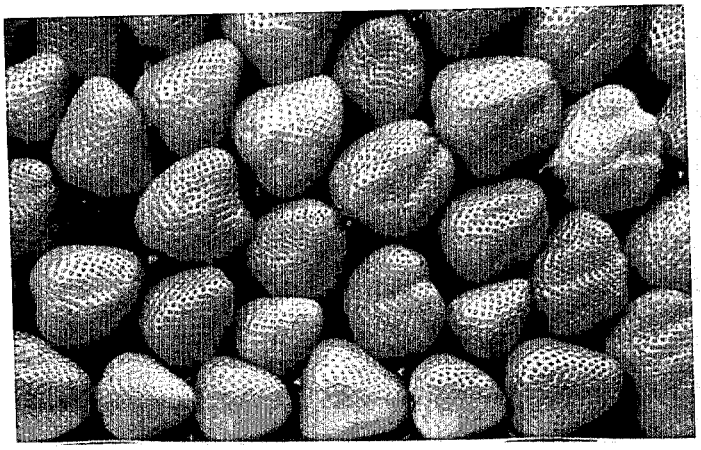
PSI 86.130
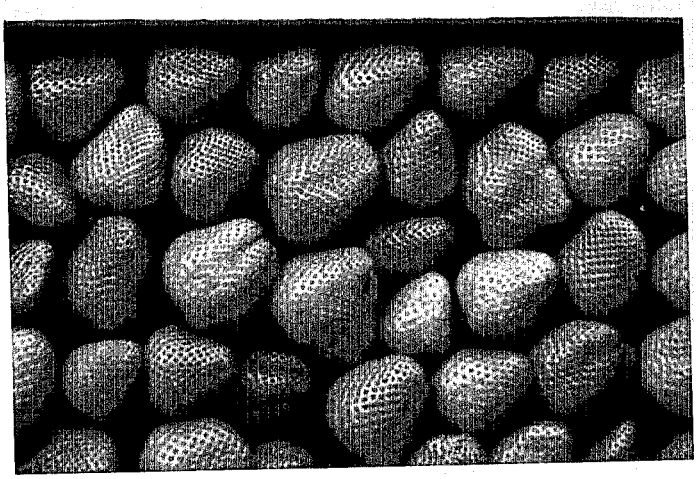

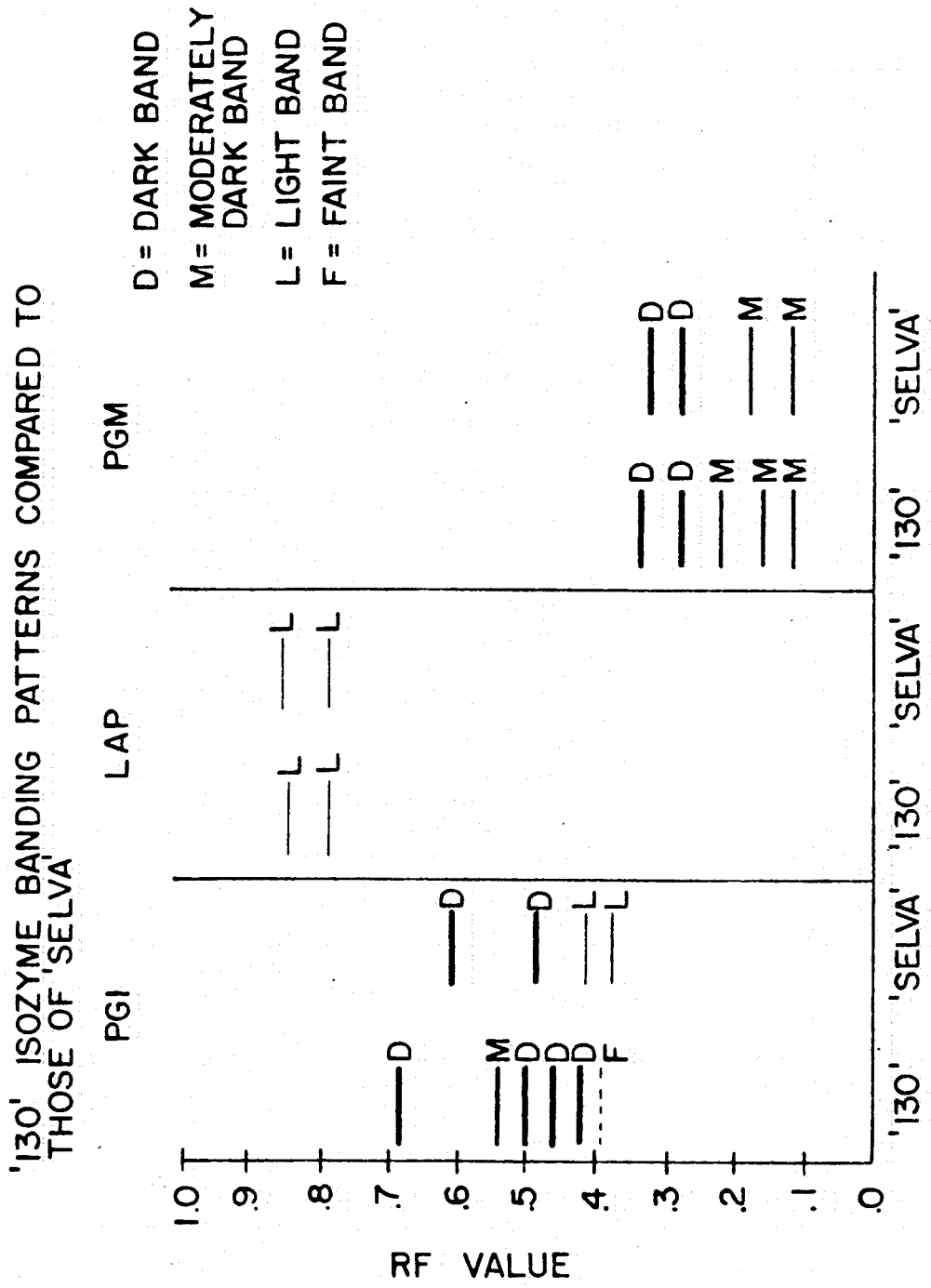
'130' ISOZYME BANDING PATTERNS COMPARED TO THOSE OF 'SELVA'
D = DARK BAND
M = MODERATELY DARK BAND
L = LIGHT BAND
F = FAINT BAND
PGI
LAP
PGM
RF VALUE
1.0
.9
.8
.7
.6
.5
.4
.3
.2
.1
0
'130'
'SELVA'
'130'
'SELVA'
'130'
'SELVA'